United States Patent
Schnaars et al.

(10) Patent No.: US 8,225,783 B2
(45) Date of Patent: Jul. 24, 2012

(54) DEVICE FOR SUPPLYING A PATIENT WITH BREATHING GAS

(75) Inventors: Henryk Schnaars, Lübeck (DE); Ahmet Türker, Lübeck (DE); Dirk-Stefan Reichert, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1240 days.

(21) Appl. No.: 11/968,321

(22) Filed: Jan. 2, 2008

(65) Prior Publication Data

US 2008/0184994 A1 Aug. 7, 2008

(30) Foreign Application Priority Data

Feb. 6, 2007 (DE) .................. 10 2007 005 819

(51) Int. Cl.
*A61M 16/01* (2006.01)
*B29C 45/14* (2006.01)

(52) U.S. Cl. ......... 128/203.12; 128/200.24; 128/202.27; 128/204.18; 128/205.25; 264/267; 264/239; 264/241; 264/259; 604/19

(58) Field of Classification Search ............. 128/203.12, 128/200.24, 204.18, 202.27, 205.24; 264/239, 264/241, 259, 267; 604/19
See application file for complete search history.

(56) References Cited

U.S. PATENT DOCUMENTS

| 3,687,137 A | * | 8/1972 | Johnson ................... 128/204.13 |
| 4,120,300 A | * | 10/1978 | Tiep ......................... 128/204.24 |
| 5,549,105 A | * | 8/1996 | Bloch et al. .............. 128/203.12 |
| 5,906,592 A | * | 5/1999 | Kriesel et al. .................. 604/132 |
| 6,044,842 A | * | 4/2000 | Pereira et al. ............ 128/202.27 |

FOREIGN PATENT DOCUMENTS

EP 0643978 B1 3/1995

* cited by examiner

*Primary Examiner* — Clinton T Ostrup
(74) *Attorney, Agent, or Firm* — McGlew and Tuttle, P.C.

(57) ABSTRACT

A device for supplying a patient with breathing gas, which has a housing provided with gas ducts and a corresponding cover (5), shall be improved such that the cover (5) can be manufactured in a simple manner and possesses good sealing properties. To accomplish the object, provisions are made for the cover (5) to consist of a one-piece, plate-like elastomer material and for groove-like depressions (10) extending in the direction of partitions (6) to be present as a seal for the gas ducts (8).

20 Claims, 5 Drawing Sheets

DEVICE FOR SUPPLYING A PATIENT WITH BREATHING GAS

CROSS REFERENCE TO RELATED APPLICATIONS

This application claims the benefit of priority under 35 U.S.C. §119 of German Patent Application DE 10 2007 005 819.7 filed Feb. 6, 2007, the entire contents of which are incorporated herein by reference.

FIELD OF THE INVENTION

The present invention pertains to a respiration system, which is provided with gas ducts and is used in anesthesia apparatuses or respirators for supplying a patient with breathing gas.

BACKGROUND OF THE INVENTION

A respiration system of the type appears from EP 643 978 B1. It comprises a housing provided with gas ducts and a cover plate, which seals the interior space of the housing against the environment. To form the gas ducts, the housing has partitions, which extend, starting from the bottom of the housing, vertically up to the top side of the housing. To seal the gas ducts, the cover plate is provided with packing gaskets (cords) or seals, which extend corresponding to the partitions. The cover plate is screwed to the housing. The packing cords lie on the front sides of the partitions. Great rigidity of both the housing and the cover plate is required for this design of the respiration system in order to obtain uniform pressing of the sealing area, because differences in height can be compensated via the packing cords to a limited extent only. The manufacture of the prior-art cover is complicated because the packing cords must be vulcanized with precision into grooves prepared in advance in the cover plate.

SUMMARY OF THE INVENTION

The basic object of the present invention is to improve a cover for a housing provided with gas ducts such that the housing can be manufactured in a simple manner and possesses hood sealing properties.

According to the invention, a device is provided for supplying a user with breathing gas. The device comprises a housing and a plate-shaped elastomeric cover formed from one piece of elastomer material. The cover covers the housing. The cover has a plurality of groove-like depressions. A plurality of partitions define gas ducts in the housing. Each partition has a front surface. The groove-like depressions of the cover seal the gas ducts. The cover has a reduced elastomer material thickness in an area of the groove-like depressions. Each groove-like depression extends along one of the partitions such that a portion of the front surface of each partition is located within one of the groove-like depressions.

The cover has a plurality of wall sections that define the groove-like depressions. Each wall section is in contact with one of the partitions to define a connection area. Each wall section has a sealing contour in the connection area with one of the partitions.

The sealing contour may comprise at least one lip portion extending along one of the partitions.

The sealing contour may comprise two lip portions with each lip portion having a different wall thickness.

One lip portion may be parallel to another lip portion with each of the lip portions extending along one of the partitions.

The cover has defined holes. Each hole is in communication with one of the gas ducts.

The device comprises a connection plate having gas ports corresponding to the holes in the cover. The connection plate braces the cover against the housing.

According to the invention, a device for supplying a user with breathing gas may comprise a respirator housing and a plurality of partition structures. The plurality of partition structures define gas ducts within the respirator housing. Each partition structure has a partition wall with an outer respirator housing cover contact surface. The partition wall defines a partition structure contour. An elastic respirator housing cover may be provided. The elastic respirator housing cover may be formed from a unitary piece of elastomer material. The respirator housing cover may have a plurality of partition covering sections defining a plurality of partition receiving grooves. Each partition receiving groove may have a partition receiving groove contour corresponding to the partition structure contour of one of the partition structures. Each partition receiving groove has an elastomer material thickness that is less than an elastomer material thickness of one of the partition covering sections. The respirator housing cover engages the respirator housing such that each partition receiving groove receives the partition wall of one of the partition structures. Each partition covering section engages the outer respirator housing cover contact surface of one of the partition structures to seal the partition structure so that the respirator housing cover seals the respirator housing.

The partition covering section may be in contact with the partition wall to define a connection area. Each partition covering section may have a sealing contour in the connection area.

The sealing contour may comprise a first protruding portion having a first wall thickness. The first protruding portion may extend along a first partition structure.

The sealing contour may comprise a second protruding portion having a second wall thickness. The second protruding portion may extend along the first partition structure. The second wall thickness may be different than the first wall thickness.

The first protruding portion may be parallel to the second protruding portion.

Each partition covering section may have elevated rim portions. Each rim portion may define a hole that is in communication with one of the gas ducts.

Each rim portion may have an elastomer material thickness that is greater than the elastomer material thickness of the partition covering section.

The device may further comprise a connection plate having gas ports. Each gas port may be in communication with one of the holes of the respirator housing cover. The connection plate may engage the respirator housing cover such that the respirator housing is pressed against the respirator housing.

According to the invention, the device for supplying a user with breathing gas may comprise a respirator device having a respirator housing with an outer housing surface and a plurality of partition walls defining gas ducts within the respirator housing. Each partition wall may have an outer contact surface. A respirator housing cover may be formed from an integral piece of elastomer material having an outer wall with an inner housing contact surface. The respirator housing cover may have a plurality of elevated partition covering sections that define a plurality of partition wall receiving recesses. Each partition wall receiving recess follows a contour of one of the partition walls. Each partition wall receiving recess may have an elastomer material thickness that is less than an elastomer material thickness of one of the elevated partition covering sections. The inner housing contact surface may engage the outer housing surface such that each partition wall receiving recess may receive one of the partition walls and each partition covering section may engage the outer contact surface of one of the partition walls so that the respirator housing cover seals the respirator housing.

The outer wall of the respirator housing cover may define a respirator housing contour. The outer housing surface may define a respirator housing contour. The respirator housing contour may be substantially identical to the respirator housing contour.

The respirator structure may have a gas inspiration port and a gas expiration port in communication with one of the gas ducts.

Each elevated partition covering section may have elevated rim portions. Each rim portion may define a hole in communication with one of the gas ducts. Each rim portion may have an elastomer material thickness that is greater than the elastomer material thickness of the partition covering section.

The device may comprise a connection plate having gas ports. Each gas port may be in communication with one of the holes of the elevated partition covering section. The connection plate may engage the respirator housing cover such that the respirator housing is pressed against the respirator housing.

The advantage of the present invention is that the cover consists of a plate-like elastomer material, which is pulled over the housing. To seal the gas ducts, groove-like depressions, which extend along the partitions and reduce the material thickness of the elastomer material in this area, are provided in the elastomer material. The depressions are pulled over the front sides of the partitions when the cover plate is placed on the housing. Good sealing is thus achieved in the connection area between the cover plate and the partitions. The pressing force exerted by the elastomer material on the partitions is increased due to the fact that the full material thickness and hence rigidity of the elastomer material is present outside the depressions. The elastomer material is thus fixed by the intrinsic stress at the partitions. The cover plate specified in the present invention can be manufactured in a simple manner according to the injection molding process. Suitable elastomers are silicone and EPDM (ethylene propylene diene monomer (M-class) rubber). Tolerances at the housing can be better compensated by the elastomer material than with a cover plate consisting of a solid material, with inserted, elastic packing cords.

The wall sections of the depressions in the connection area with the partitions advantageously also have additionally a sealing contour. This sealing contour may be a sealing lip extending along the partitions or a groove. The gas tightness between the housing and the cover is further improved by the sealing contour. It is especially advantageous that only the cover has to be replaced in case of possible damage to the sealing contour or the wall sections, while the substantially more expensive housing, which is sometimes provided with valves, can be used further.

The cover may advantageously be provided with holes in order to establish a connection to the gas ducts extending within the housing.

In addition, a closing plate with gas ports can be placed on the cover, the gas ports being located in the area of the holes of the cover.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
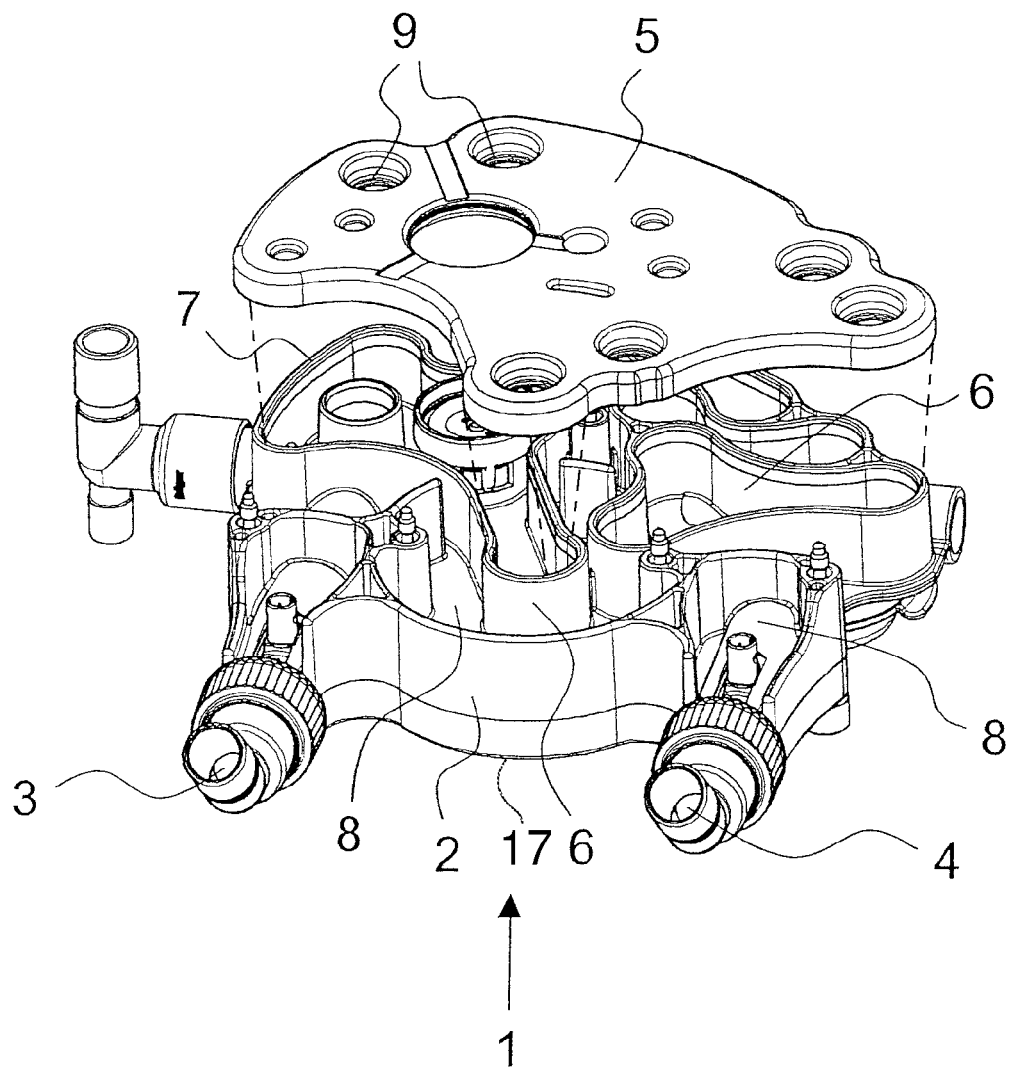
FIG. 1 is a perspective view of the closed respiration system.

Referring to the drawings in particular, FIG. 1 shows a perspective view of a closed respiration system 1 from the bottom for supplying a user, not shown more specifically, with breathing gas. The closed respiration system 1 comprises a housing 2 with an expiration port 3 and an inspiration port 4 as well as a cover 5 made of silicone, which is pulled over the housing 2. Partitions 6 are located within the housing 2 and extend from a base 17 of the housing 2 in order to form meandering gas ducts 8 between the expiration port 3 and the inspiration port 4. The partitions 6 are designed such that their front sides or edges 7 are open towards one side. Wall surfaces 16 of the partition walls 6 and the housing base 17 form the gas ducts 8 together with the cover 5. The gas ducts 8 without the cover 5 are U-shaped with the partitions 6 forming legs of the U-shape. The cover 5 is provided with holes 9 in order to make access possible to the gas ducts 8 in order for gas to be able to be drawn off from the closed respiration system 1 or fed into the closed respiration system 1. During operation, the respiration system 1 lies on a connection plate 100 (FIG. 5) with which the cover 5 is braced against the housing 2.

Figure 2:
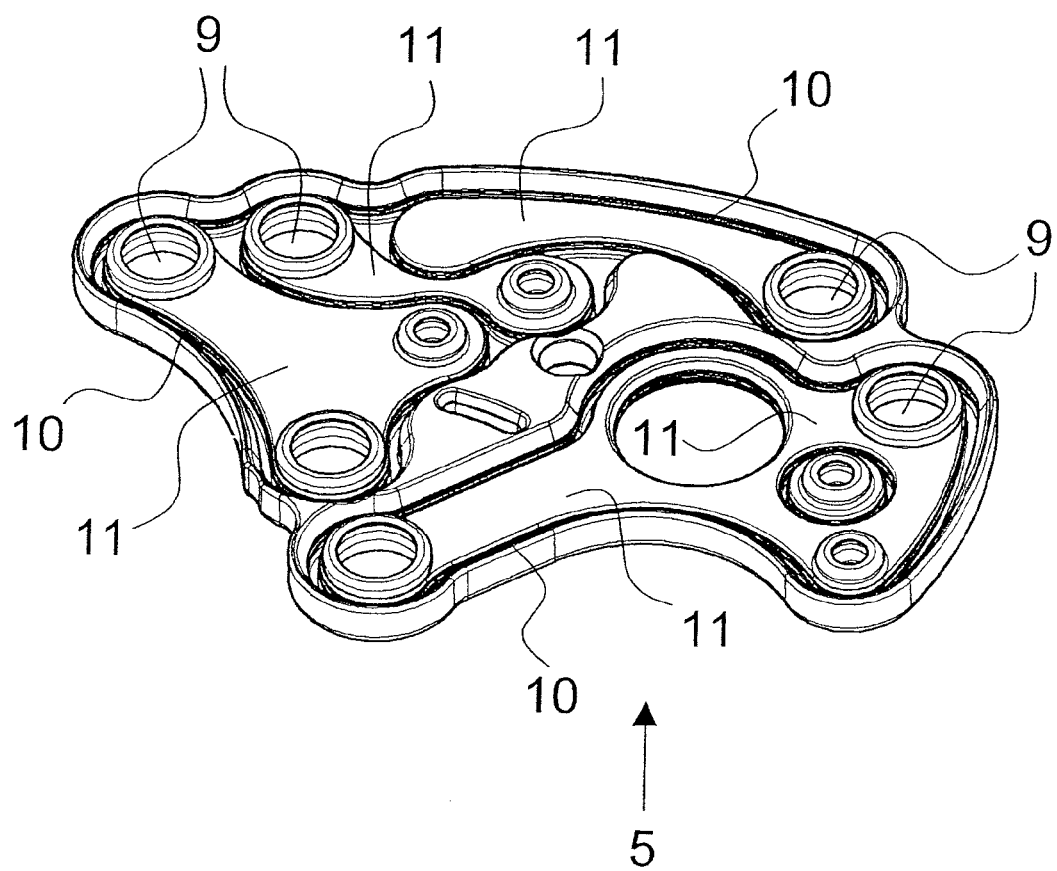
FIG. 2 is a bottom view of the bottom side of the cover.

FIG. 2 shows a view of the side of the cover 5 according to FIG. 1, which side faces the housing 2. Corresponding to the course of the partitions 6, FIG. 1, the cover 5 has groove-like depressions 10, which are recessed in the plate-like silicone material. Identical components are designated by the same reference numbers as in FIG. 1. The material thickness of the silicone material is reduced in the area of the depressions 10, whereas the full material thickness of the plate-like silicone material is present in the intermediate spaces 11 outside the depressions 10.

Figure 3:
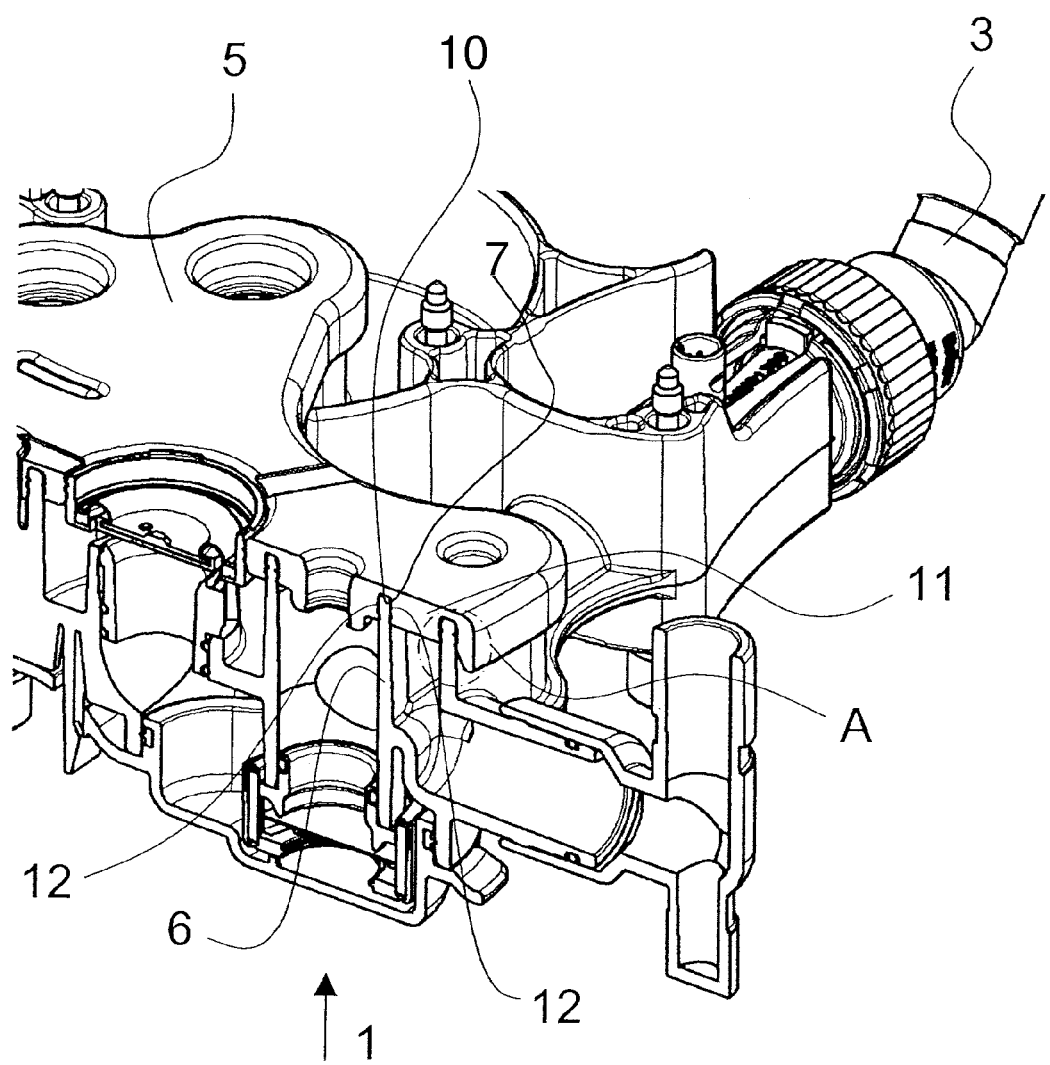
FIG. 3 is a longitudinal view through a closed respiration system with the cover attached.

FIG. 3 shows a longitudinal section through the respiration system 1 with the cover 5 attached. The wall sections 12 form sides of the depressions 10 and are in contact on both sides with the wall surfaces 16 of the partitions 6. Since the full material thickness of the silicone material is present in the intermediate spaces 11 at adjacent depressions 10, uniform contact pressing is achieved at the wall surfaces 16 of the partitions 6 because of the elastic restoring forces of the silicone material.

Figure 4:
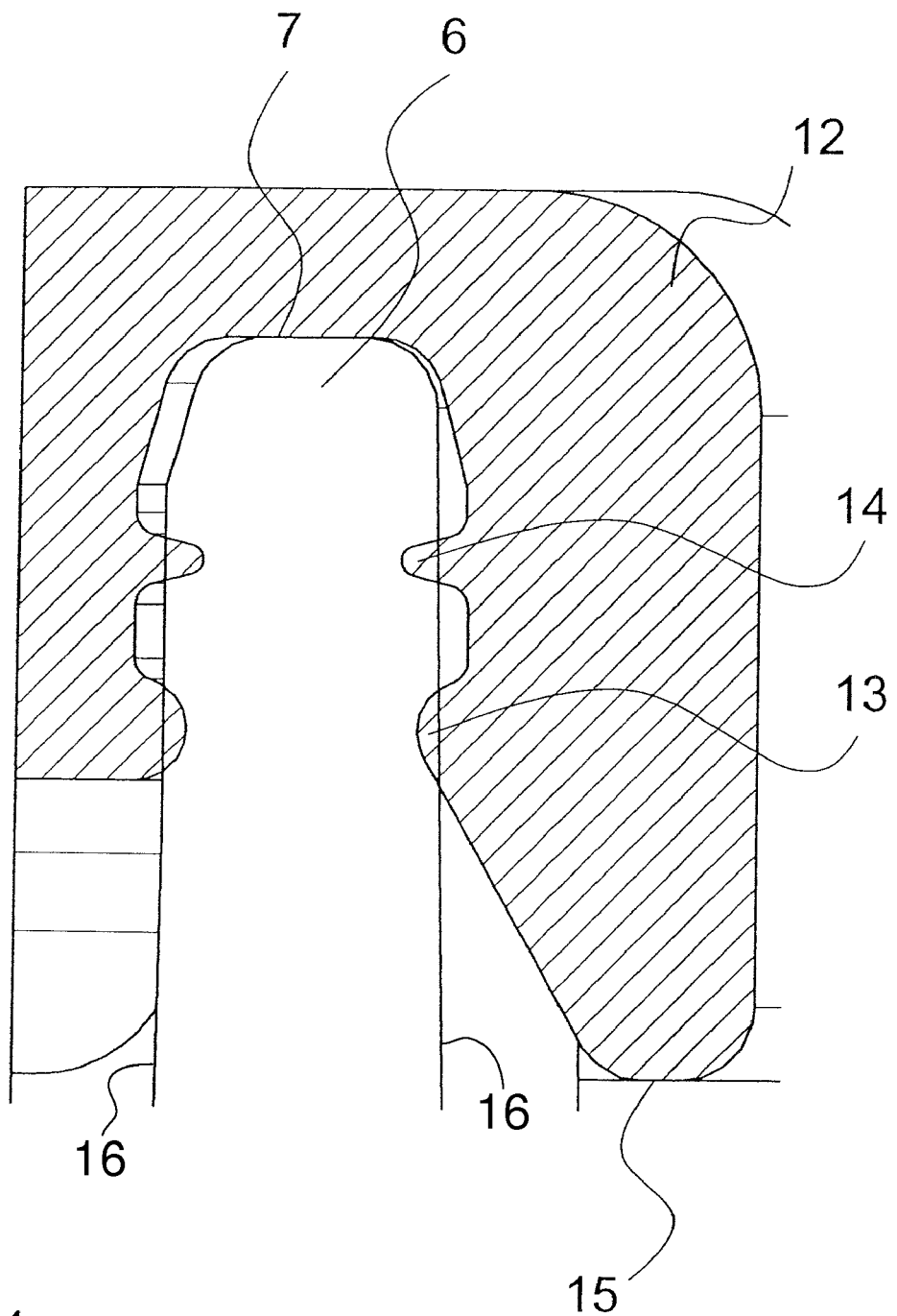
FIG. 4 is a detailed view of detail A according to FIG. 3 with a wall section of the cover.

FIG. 4 shows the enlarged detail A according to FIG. 3 with the wall section 12 at the partition 6. The wall section 12 has first and second sealing contour lips 13, 14 with different wall thicknesses, which extend as deformation zones along the partition 6. The front side 15 of the wall section 12 has a wedge-shaped design as an insertion aid in order for the cover 5 to be able to be placed simply over both the front sides or edges 7 of the partitions 6 and the housing 2. The first lip 13, which is located adjacent to the front side 15, has a great wall thickness and is used to guide the cover 5 while it is being placed on the partition 6. The second lip 14 is thin and flexible and assumes the sealing function proper. The lips 13 and 14 are shown in their un-deformed shape to show how the lips 13 and 14 will deform when the partition 6 is inserted into the groove of the cover 5.

Figure 5:
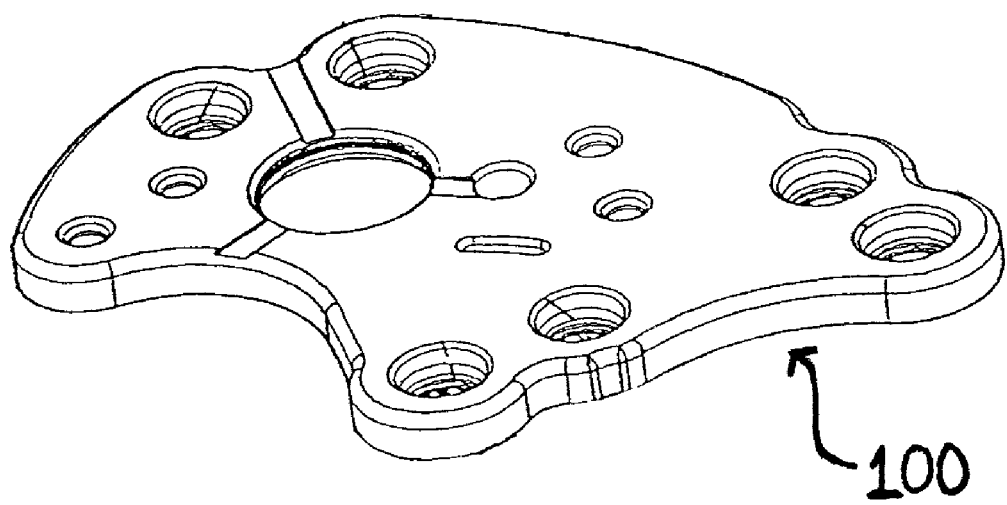
FIG. 5 is a perspective view of a connection plate.

FIG. 5 is a perspective view showing the connection plate 100 that presses or braces the cover 5 against the housing 2.

While specific embodiments of the invention have been shown and described in detail to illustrate the application of the principles of the invention, it will be understood that the invention may be embodied otherwise without departing from such principles.

What is claimed is:

1. A device for supplying a user with breathing gas, the device comprising:
   a housing;
   a plate-shaped elastomeric cover formed from one piece of elastomer material, said cover covering said housing, said cover having a plurality of groove-like depressions;
   a plurality of partitions defining gas ducts in said housing, each partition having a wall surface extending in a direction away from said plate-shaped elastomeric cover, said groove-like depressions of said cover sealing said gas ducts, said cover having a reduced elastomer material thickness in an area of said groove-like depressions, each groove-like depression extending along one of said partitions such that a portion of said wall surface of each partition is in sealing contact within one of said groove-like depressions.

2. A device in accordance with claim 1, wherein said cover has a plurality of wall sections defining said groove-like depressions, each wall section forming leg sides of said groove-like depressions and being in contact with said wall surface of one of said partitions to define a connection area, each wall section having a sealing contour in said connection area with one of said partitions.

3. A device in accordance with claim 2, wherein said sealing contour comprises at least one lip portion extending along one of said partitions.

4. A device in accordance with claim 3, wherein said sealing contour comprises two said lip portions, each lip portion having a different wall thickness.

5. A device in accordance with claim 4, wherein one lip portion is parallel to another lip portion, each of said lip portions extending along said wall surface of one of said partitions.

6. A device in accordance with claim 1, wherein said cover has defined holes, each hole being in communication with one of said gas ducts.

7. A device in accordance with claim 6, further comprising a connection plate having gas ports corresponding to said holes of said cover, said connection plate bracing said cover against said housing.

8. A device for supplying a user with breathing gas, the device comprising:
   a respirator housing;
   a plurality of partition structures defining U-shaped gas ducts within said respirator housing, each partition structure having a partition wall with an outer respirator housing cover contact surface, said contact surfaces forming leg sides of said U-shaped gas ducts, said partition wall defining a partition structure contour;
   an elastic respirator housing cover formed from a unitary piece of elastomer material, said respirator housing cover having a plurality of partition covering sections defining a plurality of partition receiving grooves, each partition receiving groove having a partition receiving groove contour corresponding to said partition structure contour of one of said partition structures, each partition receiving groove having an elastomer material thickness that is less than an elastomer material thickness of one of said partition covering sections, said respirator housing cover engaging said respirator housing such that each partition receiving groove receives said partition wall of one of said partition structures, each partition covering section engaging said outer respirator housing cover contact surface of one of said partition structures to seal said partition structure, whereby said respirator housing cover seals said respirator housing.

9. A device in accordance with claim 8, wherein said partition covering section in contact with said partition wall defines a connection area, each partition covering section having a sealing contour in said connection area.

10. A device in accordance with claim 9, wherein said sealing contour comprises a first protruding portion having a first wall thickness, said first protruding portion extending along a first partition structure.

11. A device in accordance with claim 10, wherein said sealing contour comprises a second protruding portion having a second wall thickness, said second protruding portion extending along said first partition structure, said second wall thickness being different than said first wall thickness.

12. A device in accordance with claim 8, wherein each said partition covering section has elevated rim portions, each rim portion defining a hole in communication with one of said gas ducts.

13. A device in accordance with claim 12, wherein each said rim portion has an elastomer material thickness that is greater than said elastomer material thickness of said partition covering section.

14. A device in accordance with claim 12, further comprising a connection plate having gas ports, each gas port being in communication with one of said holes of said respirator housing cover, said connection plate engaging said respirator housing cover such that said respirator housing cover is pressed against said respirator housing.

15. A device for supplying a user with breathing gas, the device comprising:
    a respirator housing including a base and a plurality of partition walls extending from said base, said base and said partition walls defining a plurality of gas ducts within said respirator housing, each partition wall having a wall surface extending from said base;
    a plate-shaped elastomeric cover formed from one piece of elastomer material, said elastomeric cover covering said respirator housing, said elastomeric cover defining a side of said plurality of gas ducts, said elastomeric cover having a plurality of wall sections defining a plurality of groove-like depressions, said plurality of wall sections and said depressions being shaped and arranged to receive said plurality of partition walls and have said wall sections of said cover form a sealing contact with said wall surfaces of said plurality of partition walls.

16. A device in accordance with claim 15, wherein:
    said gas ducts defined by said respirator housing are U-shaped, said base of said housing forming a base of said U-shaped gas ducts, said wall surfaces of said partition walls of said respirator housing forming leg sides of said U-shaped gas ducts;

said wall sections of said elastomeric cover contact said wall surfaces.

17. A device in accordance with claim 15, wherein:
each of said wall sections of said elastomeric cover include a sealing contour lip which contacts said wall surfaces of said housing to form said sealing contact.

18. A device in accordance with claim 15, wherein:
each of said wall sections of said elastomeric cover include a plurality of sealing contour lips which contact said wall surfaces of said housing to form said sealing contact.

19. A device in accordance with claim 18, wherein:
each of said plurality of sealing contour lips on a respective said wall section has a different wall thickness.

20. A device in accordance with claim 15, further comprising:
a connection plate arranged on a side of said elastomeric cover diametrically opposite said respirator housing, said connection plate bracing said elastomeric cover against said respirator housing.

* * * * *